(12) United States Patent
Stefan et al.

(10) Patent No.: US 11,826,209 B2
(45) Date of Patent: Nov. 28, 2023

(54) HOLDING DEVICE AND METHOD FOR LOCKING THE HOLDING DEVICE

(71) Applicant: Karl Storz SE & Co. KG, Tuttlingen (DE)

(72) Inventors: Jochen Stefan, Tuttlingen (DE); Sven Grüner, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 0 days.

(21) Appl. No.: 18/178,955

(22) Filed: Mar. 6, 2023

(65) Prior Publication Data

US 2023/0200932 A1 Jun. 29, 2023

Related U.S. Application Data

(62) Division of application No. 16/423,712, filed on May 28, 2019, now Pat. No. 11,622,833.

(30) Foreign Application Priority Data

May 28, 2018 (DE) .......................... 102018112682.4

(51) Int. Cl.
*F16M 13/00* (2006.01)
*A61B 90/50* (2016.01)
(Continued)

(52) U.S. Cl.
CPC .............. *A61B 90/50* (2016.02); *A61D 99/00* (2013.01); *F16M 13/022* (2013.01); *F16M 2200/022* (2013.01); *F16M 2200/06* (2013.01)

(58) Field of Classification Search
CPC ...... A61B 90/50; A61D 99/00; F16M 13/022; F16M 2200/022; F16M 2200/06
See application file for complete search history.

(56) References Cited

U.S. PATENT DOCUMENTS 3,240,516 A 3/1966 Barish
3,910,538 A * 10/1975 Baitella .................. F16M 11/14
403/56
(Continued)

FOREIGN PATENT DOCUMENTS

CH 608874 A5 1/1979
CH 645529 A5 10/1984
(Continued)

OTHER PUBLICATIONS

National Industrial Property Institute, Preliminary Search Report, Application No. FR1905557, dated Nov. 30, 2022.
(Continued)

*Primary Examiner* — Amy J. Sterling
(74) *Attorney, Agent, or Firm* — Honigman LLP

(57) ABSTRACT

The invention relates to a holding device 020 for human-medicine or veterinary-medicine applications comprising: a joint between a proximal holding segment 001 and a distal holding segment 017; wherein one axially displaceable thrust element 002, 016 in each case is arranged in the holding segments 001, 017; wherein the joint has a tightening bolt, which defines the pivoting and tightening axis, and has deflection elements, by means of which a thrust force, acting relative to the axis, of the proximal thrust element 002 is deflectable to lock the joint onto the tightening axis and to displace the distal thrust element 016; and wherein the deflection elements comprise at least one ramp system with a wedge body 008. The invention further relates to a holding system comprising the specified holding device and a method for locking the joint of the specified holding device 020.

20 Claims, 7 Drawing Sheets

(51) Int. Cl.
*F16M 13/02* (2006.01)
*A61D 99/00* (2006.01)

(56) References Cited

U.S. PATENT DOCUMENTS

| | | | | |
|---|---|---|---|---|
| 4,236,844 | A * | 12/1980 | Mantele | F16M 11/14 403/55 |
| 4,431,329 | A * | 2/1984 | Baitelle | F16M 11/2007 403/55 |
| 5,261,590 | A * | 11/1993 | Tsai | F16M 11/14 228/55 |
| 6,575,653 | B1 * | 6/2003 | Krauter | A61G 13/101 403/55 |
| 10,788,160 | B2 | 9/2020 | Elias | |
| 11,622,833 | B2 * | 4/2023 | Stefan | F16M 13/022 403/92 |
| 2014/0084761 | A1 | 3/2014 | Scott et al. | |
| 2017/0276291 | A1 * | 9/2017 | Subratie | F16M 13/02 |
| 2018/0116758 | A1 | 5/2018 | Schlosser et al. | |

FOREIGN PATENT DOCUMENTS

| | | | |
|---|---|---|---|
| CN | 105179895 | A | 12/2015 |
| WO | 2013080462 | A1 | 6/2013 |
| WO | 2016160272 | A1 | 10/2016 |

OTHER PUBLICATIONS

United Kingdom Examination Report, Application No. GB1907142.2, completed Nov. 15, 2019. 6 pages.
German Search Report, Application No. 10 2018 112 682.4, dated Jan. 16, 2019. 7 pages.

* cited by examiner

HOLDING DEVICE AND METHOD FOR LOCKING THE HOLDING DEVICE

CROSS-REFERENCE TO RELATED APPLICATION

This application is a divisional of U.S. application Ser. No. 16/423,712 filed May 28, 2019, which claims priority of German Patent Application No. 102018112682.4 filed on May 28, 2018, the contents of which are incorporated herein by reference in their entirety.

TECHNOLOGICAL BACKGROUND

The invention relates to a holding device having a lockable joint between two holding segments for medical applications, for example for holding or positioning a surgical instrument. The invention further relates to a holding system with the specified holding device and a method for locking and releasing the joint of the specified holding device.

One-armed or multi-armed holding devices or holding systems for medical instruments with passive or active guiding are known. In this case, holding devices or systems for guiding instruments are required in particular in minimally invasive surgical interventions, in order to relieve a surgeon, assistant or other operator from the tiring work of holding. Such holding devices can be employed to hold a surgical instrument such as a manipulator, an optical aid such as an endoscope, a clamp or the like at its distal end. Furthermore, mechatronic assistance systems can also be combined with a holding device. In this case, it is important that attached devices or systems can be handled simply and that the holding system enables disruption-free operation. When using instruments, it is moreover advantageous to provide the surgeon with a large number of degrees of freedom.

A manually adjustable holding device is known from CH 645 529, which has two arms which are pivotable relative to one another and which are connected by a central joint in an articulated manner. The arms can be locked at the central joint using a tightening member in the form of a hand lever via displaceable tightening sleeves or sockets. A disadvantage of this known device is that two hands are generally required to release and lock the holding system. The expenditure of force for tightening is comparatively high as a result of the friction losses in the central joint. There is therefore the need to increase the effectiveness in the flow of force by reducing the friction losses.

Alongside the relatively high friction losses, a further disadvantage of the manually adjustable holding device according to CH 645 529 is that the transmission relationship, i.e. the relationship in which the force and the path are implemented, can only be improved to a limited extent by exchanging tightening sleeves with steeper run-on surfaces. There is namely the problem that, if the run-on surfaces of a tightening sleeve are configured too steeply, they lead to an excessively large self-inhibition in the event of locking. For example, in the event of angles over 70° such a large degree of self-inhibition arises that the holding device can no longer be released after locking.

The aim of the present invention is to overcome the specified disadvantages and to provide a holding device which is simple to operate and which can be locked or released without a hand lever or a hand screw on the tightening axis of the joint of the holding device. The holding device should in particular be lockable through pressure or introduction of force from the proximal side on an open proximal arm segment or holding segment.

A further aim of the invention is to improve the effectiveness when deflecting force in the joint of the holding device. Finally, instruments should remain controllable when the holding device is in a released position and should not move in an unpredicted manner after release or after assuming the release position.

According to a first aspect of the invention, a holding device for human-medicine or veterinary-medicine applications is provided, comprising a joint between a proximal holding segment and a distal holding segment; wherein at least one axially displaceable thrust element in each case is arranged in the holding segments, wherein the joint has a tightening bolt, which defines the pivoting and tightening axis, and has deflection elements, by means of which a thrust force, acting relative to the axis, of the proximal thrust element is deflectable to lock the joint onto the tightening axis and to displace the distal thrust element, and wherein the deflection elements comprise at least one ramp system with a wedge body.

With the aid of the deflection elements comprising a ramp system, the tightening bolt can be displaced by means of the introduction of force from the proximal side such that the holding device can be brought from a released position or release position into a locked position or locking position. When the holding device is in the release position, the holding segments can be pivoted relative to one another such that a distal connection part or an attachable instrument is brought into a desired position. The joint of the holding device can then be locked by means of the tightening bolt and the holding segments can thus be fixed in the adjusted position.

In the locking process, the at least one axially displaceable proximal thrust element serves to introduce force proximally, while the at least one axial distal thrust element is displaceable outwards away from the joint in order to apply force distally. The force deflected by 90° by the tightening axis in the direction of the distal thrust element can in turn be used to fix or lock a distal connection part or instrument and thus support a surgeon or other operator.

The force can advantageously be introduced proximally via the proximal thrust element, so that manual locking by means of a tightening lever at the central joint of the holding device is no longer required.

Friction losses can be reduced through the use of a ramp system with a wedge body, which preferably has inclined wedge surfaces, on both sides and the effectiveness can be improved up to threefold compared to conventional force transmission mechanisms which use neither a wedge body nor a sliding body.

According to a further aspect of the invention, the at least one ramp system comprises a base plate which is penetrated by the tightening bolt and which has at least one base ramp surface, and a mating plate which is firmly connected to the tightening bolt and which has at least one mating ramp surface, wherein the wedge body which is acted on by force is displaceable between the ramp surfaces and is configured to move the mating plate relative to the base plate supported on a housing of the joint, and thus to deflect the force by 90°.

The tightening bolt penetrates the base plate and the at least one ramp surface of the base plate faces an allocatable wedge surface of the wedge body. This design contributes to an optimisation of the space required for the ramp system in the central joint of the holding device. During its displacement, the wedge body is displaceable both perpendicular to the tightening axis and axially relative to the tightening axis.

The component of the displacement path in the axial direction is limited on one side by the base plate supported on the housing, such that the axial displacement from the release position into the locking position takes place in the direction of the movable mating plate, in order to move this together with the tightening bolt for the purpose of locking.

According to a further aspect of the invention, the component, which is directed perpendicular to the tightening axis, of the displacement path of the wedge body between the release position and the locking position is definable by the length of a central elongated hole of the wedge body.

The elongated hole forms a through-aperture of the wedge body for the tightening bolt, so that the wedge body forms a substantially oval hollow cylinder, the base surfaces or annular surfaces of which each have one or two opposing wedge surfaces. The elongated hole is configured such that it enables a displacement of the wedge body both perpendicularly and axially relative to the tightening bolt. Depending on the size of the length or breadth of the elongated hole, the displacement movement of the wedge body 008 can take place with play with respect to the tightening bolt 010 or can be conducted partly through at least one wall of the elongated hole. The ends of the elongated hole of the wedge body can in this case adopt a stopping function and/or a guiding function, in order to limit the displacement perpendicular to the tightening axis and/or to guide the wedge body along the tightening axis. A possible friction in the displacement movement between at least one of the walls of the elongated hole of the wedge body and the tightening bolt should be kept low through the configuration of relatively small contact surfaces, in order to enable a low-friction lateral movement of the wedge body on the tightening bolt.

According to a further aspect of the invention, at least one base ramp surface and the at least one mating ramp surface engage one another by the assignable wedge surfaces of the wedge body in each case via at least one sliding body.

Through the additional use of sliding bodies, the friction can be significantly decreased between the respective interacting sliding partners, i.e. the wedge surfaces and assignable ramp surfaces.

According to a further aspect of the invention, the sliding bodies are rolling bodies in the form of spheres, cylinder rollers or barrel rollers.

In this manner, the friction between the interacting surfaces can be reduced to as small a degree as possible. Particularly advantageous in this case are barrel rollers, with the surface shell having a convex configuration in each case. These barrel rollers not only have a smaller bearing surface compared to cylinder rollers, but rather also enable automatic centring on arch-shaped or curve-shaped ramp or wedge surfaces.

According to a further aspect of the invention, the base ramp and/or the mating ramp each have two at least sectionally cylinder-segment-shaped recesses, which each have a track surface curved towards the respective sliding body as a ramp surface.

In this manner it is possible to provide geometric relationships and automatic centring surfaces which are favourable to the sliding body, in order to promote low-friction and reliable operation of the ramp system. Not only the ramp surfaces, but also the wedge surfaces which interact with them, should have tracks which are arched or curved in such a way as to enable the surfaces to slide on one another with low friction. The use of sliding or rolling bodies in curved or arched tracks of the interacting surfaces can in this case achieve a significant reduction in friction compared to conventional linear bearings.

According to a further aspect of the invention, the displacement of the distal thrust element can be used for the frictional locking of a distal connection part and/or a medical instrument.

In this manner, a medical instrument such as a surgical instrument or optical aid or the like can be held by the holding device via a connection part or directly. In order to suit different demands in various surgical scenarios, the length of the holding segments and the holding force can be varied. In this case, relatively short holding devices having a length of approximately 15 cm to 20 cm length per holding segment should be envisaged if relatively high holding forces of at least 3 kg, preferably 5 kg, are to be provided.

According to a further aspect of the invention, the distal connection part is a hand joint that can be coupled to a handle which has at least one actuation element in order to optionally lock or release the joint.

With the aid of a distal handle and in particular the actuation element, the surgeon or another operator can easily, i.e. with only one hand, bring about the locking or releasing of the holding device.

According to a further aspect of the invention, the housing of the joint is configured in two parts and the ramp system is arranged in the proximal and/or distal housing half.

Providing the ramp system in the proximal side of the joint housing is particularly advantageous if high forces are necessary to lock the central joint. In the case of this arrangement of the ramp system, the proximally introduced force can be strengthened approximately threefold compared to conventional tightening mechanisms without a wedge body and the path is reduced to one third. Through the ramp system, relatively short displacement paths can cause very high clamping or locking forces to be conducted onto the central joint. In this manner it can be ensured that a locking of the joint takes place reliably and that both housing halves are pressed onto one another with a high force.

Depending on the force/path relationships desired, a further ramp system with a wedge body and sliding bodies can be arranged in the distal housing half as an alternative to or in addition to the arrangement in the proximal housing half.

According to a further aspect of the invention, the holding segments can be pivoted relative to one another via the joint by a pivot angle of up to 340°.

Limiting the rotation around the joint main axis to 340° is in particular advantageous, if a cable is guided from the first to the second holding segment. In this manner it is advantageously possible to prevent technical malfunctions or breaking of a cable attached to the holding device.

The limiting of the pivotability to a maximum of 340° can be realised by means of an anti-rotation pin and a suitable circumferential groove with stops which are each arranged in a housing half of the central joint of the holding device. The stops are formed as radially running stop surfaces in the circumferential groove or respectively at the end of a partly annular circumferential groove and can limit the rotating angle to the specified 340°, which gives a dead angle of 20°. Dead angles of at least 20° are to be preferred here, as these can be produced more robustly and therefore have an advantageous effect on the lifespan of the holding device.

According to a further aspect of the invention, the deflection elements further comprise a ramp socket which has a curved ramp surface for a sliding body, wherein the ramp socket is rotatably connected to the tightening bolt and is displaceable by displacing the relative location of the tightening bolt along the tightening axis and is engaged with a thrust element via the sliding body in order to deflect force.

In this way, the ramp system can be combined with a ramp socket. This is advantageous if significantly less force is meant to be conducted into or out of one housing half than is meant to be conducted into or out of the other housing half. For example, the ramp socket can be arranged in the distal housing half if significantly less force is required for the clamping of a distal connection part than for the clamping of the joint of the holding device.

According to a further aspect of the invention, the thrust elements are configured as one-part or multi-part thrust rods.

In other words, the thrust elements can either be configured in one piece or consist of separate parts. One or two thrust elements thus serve as thrust rods or so-called pressure-rams and can for example be pushed loosely into the respective open holding segments and can thus be exchanged simply when necessary. The individual thrust elements and the remaining parts of the holding device are suitable for machine cleaning and disinfection and steam sterilisation in autoclaving.

According to a further aspect of the invention, the thrust rod end which interacts with the sliding body of the ramp socket has a ramp surface.

Advantageously, that end of the distal thrust rod which is close to the joint has a ramp surface, through the angle of which, together with the angle of the ramp socket, it is possible to determine the relationship in which the force and the path are implemented. The loosely usable thrust rods with ramp surfaces, which are also called ramp rams, can simply be taken out of the holding segment and be replaced by a ramp ram with a different angle depending on requirements.

According to a further aspect of the invention, the proximal housing half comprises the ramp system and the distal housing half comprises the ramp socket with a sliding body configured as a cylindrical or barrel-shaped rolling body.

This is advantageous if significantly less force is required for the clamping of a distal connection part, for example, than for the clamping of the joint of the holding device.

According to a further aspect of the invention, the joint has an end cap which can be removed from the proximal housing half in order to enable a manual displacement of the relative location of the tightening bolt over the proximal end of the tightening bolt.

If the end cap is taken off at the joint, it is possible to manually displace the tightening bolt at its proximal end by means of suitable tools without introducing force at the proximal holding segment. In this manner, the holding device can be set manually and a fine adjustment can be performed, which are generally carried out by the manufacturer of the holding device or by maintenance personnel.

According to a further aspect of the invention, the tightening bolt has, at the proximal end, a thread for a nut which is configured to manually displace the relative location of the tightening bolt.

This nut can be operated simply with a conventional tool such as a screwdriver and simplifies necessary setting or maintenance.

According to a further aspect of the invention, the housing of the joint and/or the holding segments have at least one receptacle for spring means.

The specified spring means can advantageously guarantee a certain residual inhibition and thus free holding segments of the holding device or of joints, which are attached to the distal holding segment, can be prevented from flapping around in an uncontrolled manner.

According to a further aspect of the invention, the proximal holding segment can be connected at its proximal end to a clamping device, by means of which the thrust element of the proximal holding segment can be displaced to lock and release the joint of the holding device.

A spindle drive or the like is provided as a drive unit for the relative displacement of the proximal thrust element. These drives allow simple controlling of the relative displacement, since it can be actuated both by one hand and also advantageously by means of a motor.

According to a further aspect of the invention, the holding device and the clamping device can be connected to one another by means of a coupling device.

The coupling device is configured such that it can rapidly couple the holding device to, or decouple it from, the clamping device. The coupling device is in this case configured such that it cannot be released while in operation, even if large forces exert an action during the operation of the holding device.

According to a further aspect of the invention, a cable is guided from a proximal actuation element at a handle, which is attached to the distal holding segment, along the holding segments, bypassing the joint, and is connected to a drive unit in order to axially displace the proximal thrust element of the holding device by means of a driveable spindle of the clamping device.

In this manner, the cable can be used in order to be able to connect a proximal drive unit for the proximal introduction of force to a distal actuation element. The cable guided along the holding segments generally bypasses the joint of the holding device in a loose loop. In the case of an embodiment of the holding device without limitation of the pivotability of the holding segments, there is the danger here of the cable twisting or being overloaded and thus of the functionality of the cable being damaged. In order to lastingly protect the cable from overloading or breaking, the rotatability of the joint of the holding device or of the holding segments relative to one another to at least 340° is to be envisaged when a cable is guided along the holding segments.

Furthermore, a method for human-medicine or veterinary-medicine applications for locking and releasing a joint of a holding device having two holding segments which are pivotable relative to one another is provided. The method comprises the following steps: displacing an axially displaceable thrust element in a proximal holding segment, deflecting the proximal thrust force of the proximal thrust element onto the tightening axis of the tightening bolt of the joint, in order to lock the joint, and deflecting the tightening force onto the distal thrust element of the distal holding segment, in order to lock a distal connection part and/or a medical instrument by displacing the distal thrust element away from the tightening axis, wherein the deflection takes place by means of deflection elements comprising at least one ramp system with a wedge body.

BRIEF DESCRIPTION OF THE FIGURES

Further advantages and features of the invention emerge from the following description of exemplary embodiments on the basis of the figures. In the drawings.

The depictions are schematic and are not necessarily true to scale. Furthermore, they do not show all details but rather partly restrict themselves to the depiction of the details which are significant to the invention and of further features which facilitate the explanation and description of the invention. Identical elements in the various figures are labelled with identical reference numbers.

DETAILED DESCRIPTION OF THE FIGURES

Figure 1:
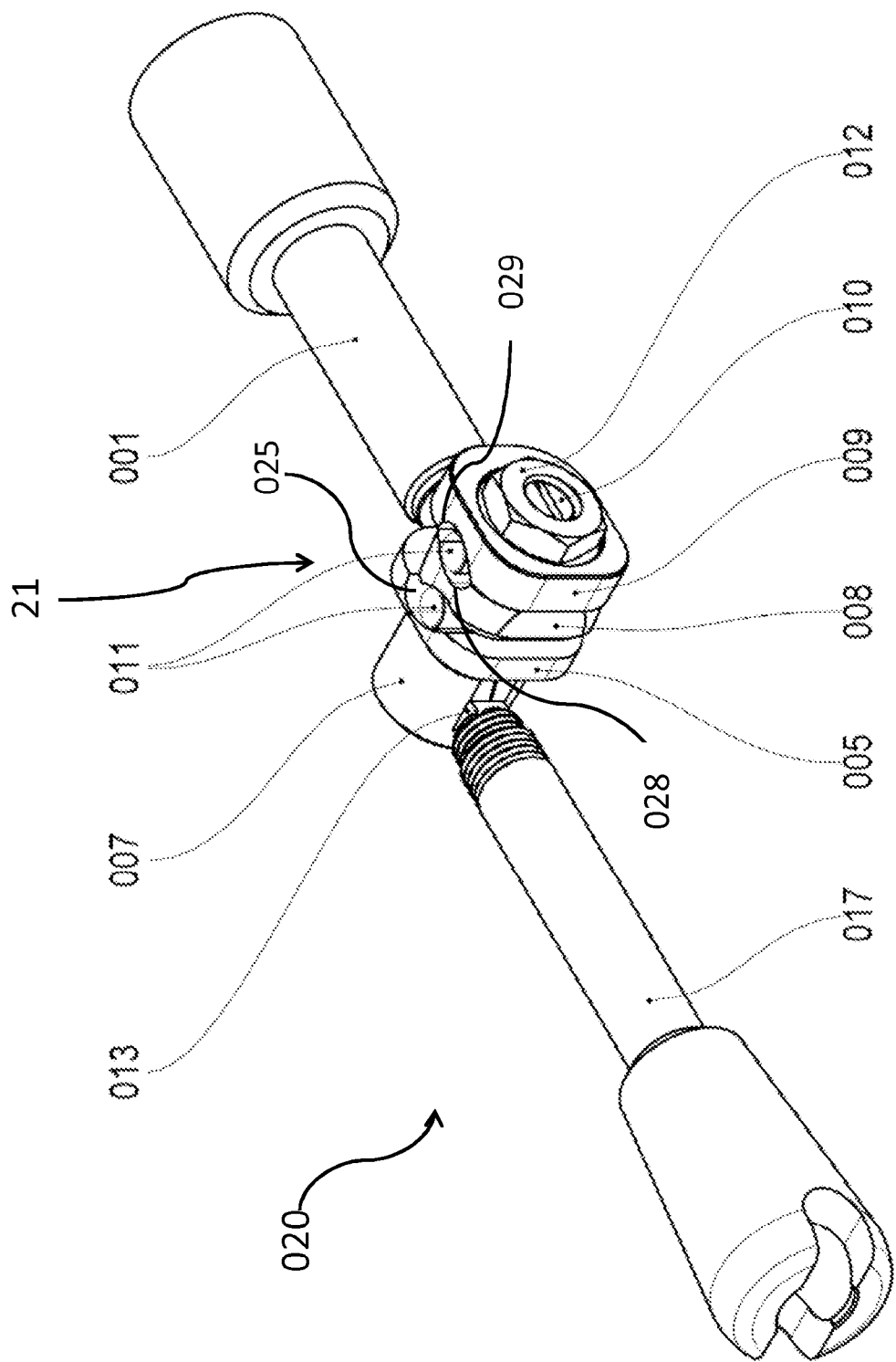
FIG. 1 shows a perspective view of an embodiment of a holding device according to the invention.

The perspective view from FIG. 1 shows an embodiment of a holding device 020, according to the invention, for human-medicine or veterinary-medicine applications. This holding device 020 consists of a proximal holding segment 001 and a distal holding segment 017, with a joint 021 connecting the proximal and distal holding segment 017. The joint 021 is depicted in a simplified manner, i.e. without a housing, and shows the significant components required for conducting force or deflecting force.

The two holding segments 001 and 017 are pivotably borne by means of the lockable joint 021. The ramp system has a base plate 005 penetrated by a tightening bolt 010. The mating plate 009 is likewise penetrated by the tightening bolt 010, but, in contrast to the base plate 005, is firmly connected to the tightening bolt 010. Both the base plate 005 and the mating plate 009 have at least one ramp surface (29, 25), which interact with the wedge surfaces 028 of a wedge body 008. For this purpose, the wedge body 008 is arranged between the base plate 005 and the mating plate 009.

The wedge body 008 is configured as a hollow cylinder and has at its two base surfaces at least one wedge surface 028, which on one side is situated opposite the at least one base ramp surface 025 and which on the other side is also assignable to the at least one mating ramp surface 029. The ramp surfaces 025 and 029 engage with the assignable wedge surfaces 028 of the wedge body 008 via sliding bodies 011.

The tightening bolt 010 has at its proximal end a thread, which is not shown here, for a nut 012, by means of which it is possible to manually displace the relative location of the tightening bolt 010 for adjustment or maintenance of the holding devices. As a general rule, this adjustment possibility with the nut 012 is not used for the normal operation of the holding device, since the application of force to lock the joint 21 takes place on the side of the tubular proximal holding segment 001.

The distal end of the tightening bolt 010 is not visible in FIG. 1, because it is arranged in a ramp socket 007. The ramp socket 007 engages the thrust element (not shown in FIG. 1), which runs axially in the holding segment 017, via a sliding body 013. The holding segment 017 has at its end a thread, in order to be able to be connected to the distal housing half (not shown here).

Figure 2A:
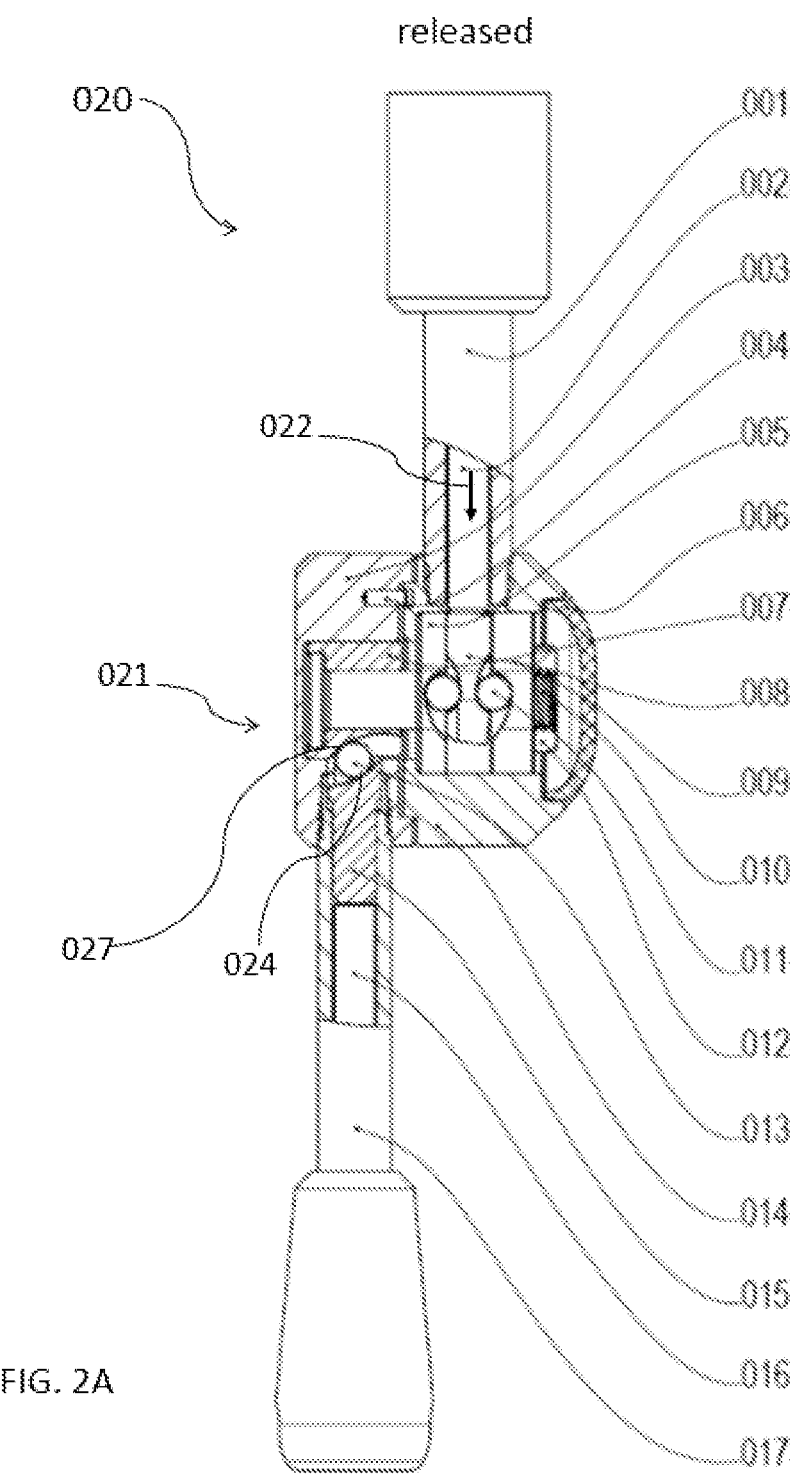
FIG. 2A shows a schematic plan view of a further embodiment of a holding device according to the invention with a housing and a partial sectional view in the released position.

FIG. 2A shows a schematic plan view of the holding device 020, in which the joint 021 and the ends of the holding segments 001 and 017 which are close to the joint are shown in a partial sectional view and, in addition, the two housing halves 003, 014 of the joint 21 are shown. FIG. 2A shows in the partial sectional view that the housing of the joint 021 is configured in two parts. In this case, the proximal housing half 014 has the ramp system and the distal housing half 003 has the ramp socket 007.

The partial sectional view of the distal holding segment 017 shows that the holding segment 017 and the distal housing half 003 are connected via a thread. Furthermore, the partial sectional view shows that two axially displaceable thrust elements 015 and 016 are arranged in the holding segment 017. The ramp socket 007 engages the thrust element 015 via the sliding body 013. The thrust element 015 has ramp surface 024 which is curved relative to the sliding body 013. The thus friction-optimised ramp surface 024 of the thrust element 015 or ramp ram 015 forms the frictional surface with the sliding body 013. On the other side of the sliding body 013 there is arranged a ramp surface 027 of the ramp socket 007. In order to support automatic centring in the ramp tracks, the sliding body 13 is preferably configured as rolling bodies in the form of barrel rollers.

Further sliding bodies 011 are located in the ramp system in the proximal housing half 014. The base ramp 005 and mating ramp 009 each have sectionally circular-segment-shaped recesses which each have a track surface curved towards the respective sliding body 011. The curved tracks likewise serve to automatically centre the sliding bodies 011. By using the sliding or rolling bodies in the form of barrel rollers, it is possible to reduce the friction, and to support automatic centring on arched tracks.

In the depicted release position or released position of the holding device, the sliding bods 011 are arranged at the proximal ends of the ramp surfaces and the wedge body 008 is substantially perpendicular to the tightening axis. Through the displacement of the thrust element 002 in the distal direction, the wedge body 008 can be displaced both distally and axially. A possible displacement or a displacement path from the shown release position of the thrust element 002 in the distal direction is indicated by the arrow 022.

In the shown released position or release position, the two housing halves 003 and 014 are movable relative to one another, around the tightening axis. The holding segments 001 and 017 are thus also movable relative to one another around a large pivot angle. The cylindrical pin or securing pin 004 limits the pivotability to a range of preferably 340° and thus prevents an endless rotation of the holding segments 001, 017 relative to one another.

A limitation of the pivotability is advantageous if a cable is guided along from the first to the second holding segment and if this does not incur damage from overloading as a result of the restricted rotatability. If no guiding of cable along the holding device is envisaged, but rather a different type of signal transmission such as radio control, it is possible to dispense with the mechanical limitation of the cylindrical pin 004 and an infinite rotatability of the holding segments 001, 017 relative to one another is made possible.

The end cap 006 closes the access to the nut 012 and the proximal end of the tightening bolt 010. If the end cap 006 is taken off at the joint 021, it is possible to manually displace the tightening bolt 010 at its proximal end by means of suitable tools without applying force at the proximal holding segment. The adjusting takes place by means of a screwdriver or the like, for example. The manual adjustment is generally only envisaged prior to the first entry into operation and for later maintenance, if necessary. In this case it is advantageous if it is envisaged that the adjustment is only permitted to take place without any load, i.e. when the tightening bolt 010 is released. The distal end of the tightening bolt 010 is generally located under the cover 006 after the holding device 020 has been supplied to the user. This is intended to prevent the user from independently altering the setting required for operation.

If the thrust element 002 is displaced in the distal direction in accordance with the arrow 022, both the joint 021 and the distal medical instrument, which is operatively connected via the thrust elements 015 and 016, can be jointly locked. This is carried out by means of the tightening bolt 010 arranged perpendicular to the holding segments 001 and 017. Its mode of operation shall be explained hereafter with reference to FIG. 2B.

Figure 2B:
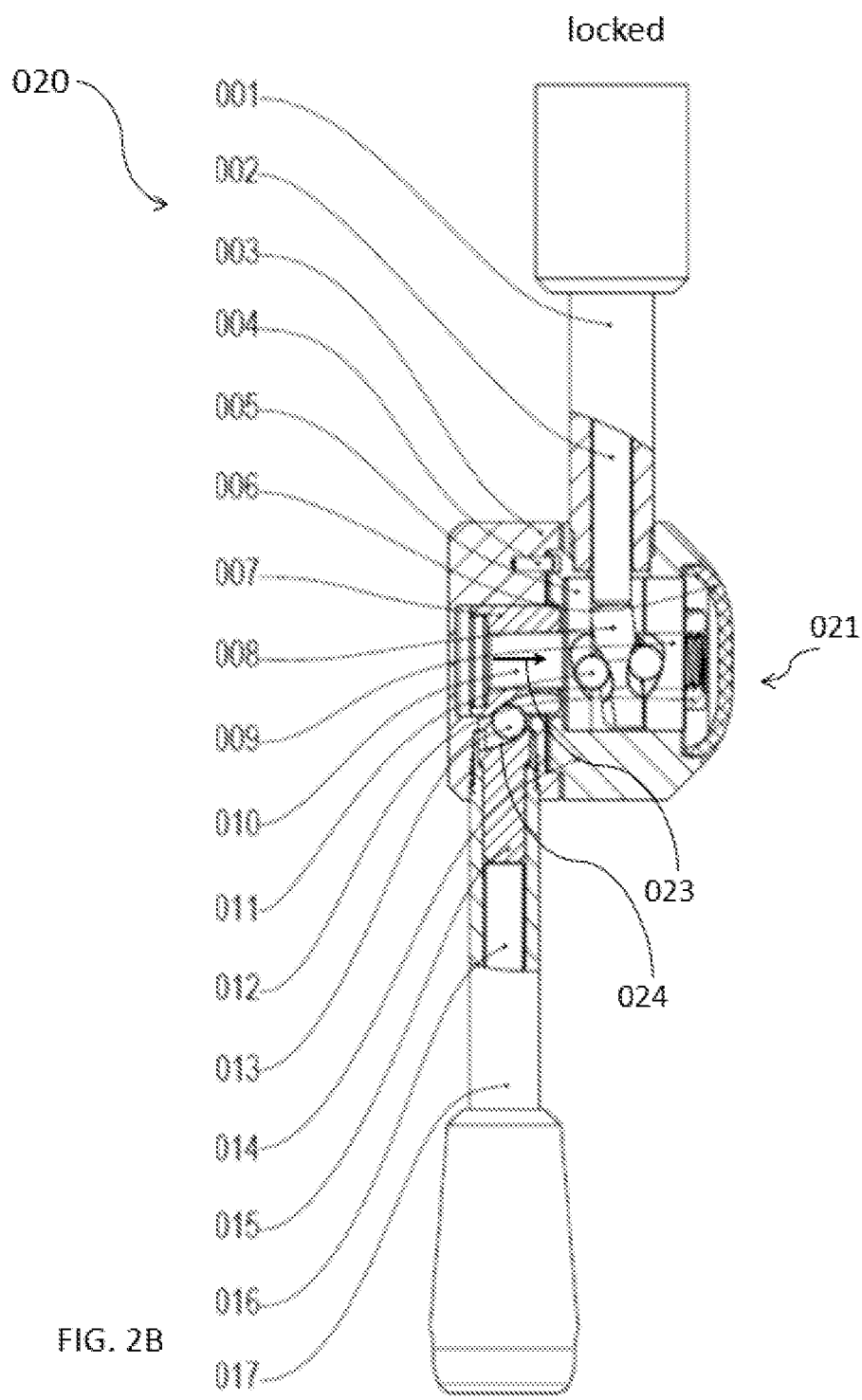
FIG. 2B shows a schematic plan view of the holding device shown in FIG. 2A in the locked position.

FIG. 2B depicts the locked position or locking position, with identical elements being identified using the same reference numbers. By applying force at the proximal side of the holding segment 001, the thrust element 002 has been displaced into the locking position in direction of the central joint 021, so that the wedge body 008 has moved between the ramp 005 and the mating ramp 009 out of the release position into the locking position. When force is applied, the wedge body 008 is moved such that it pushes respectively away from the housing and from one of the mating ramp plates 009 via the sliding body 011. In this case, the mating ramp 009 is firmly connected by the tightening screw 010.

The displacement path of the wedge body 008 from the release position to the locking position has both a component perpendicular to the tightening axis and along the tightening axis. By means of the wedge body 008, the proximal force introduced by the thrust element 002 can be deflected by 90° into the tightening axis, in order to thus clamp the joint 021. In the locking position, a proximal side of the wedge body 008 rests on the base plate, while the distal inclined end of the wedge body 008 can come to a stop on the distal housing wall of the housing half 014, this distal housing wall running parallel to the tightening axis. The wedge body 008 thus assumes the inclined position shown in FIG. 2B with respect to the tightening axis. The wedge body 008 can in this case advantageously be used in order that the resulting counter-forces in the locking process during the lateral deflection of force can be directly introduced into the housing.

The introduced force can additionally be deflected by 90° by means of the ramp socket 007, the ramp socket 007 being rotatably connected to the tightening bolt 010. In order to get into the locking position shown, the ramp socket 007 has been displaced together with the tightening bolt 010 along the tightening axis in the proximal or axial direction (arrow 23). The arrow 23 indicates the axial displacement path of the tightening bolt 010 from the release position to the locking position.

The diverted force is transmitted, via the ramp ram 015 or thrust element 015 with ramp surface 024, onto the distal thrust element 016, in order, through the outward displacement of the thrust element 016, to be able to lock a joint or medical instrument attached thereto. Through the use of curved ramp surfaces and sliding bodies 013, the deflection of force can be performed with relatively little friction and, through the distal displacement generated, downstream joints connected to the thrust elements 015 or 016 can be locked.

Figure 3A:
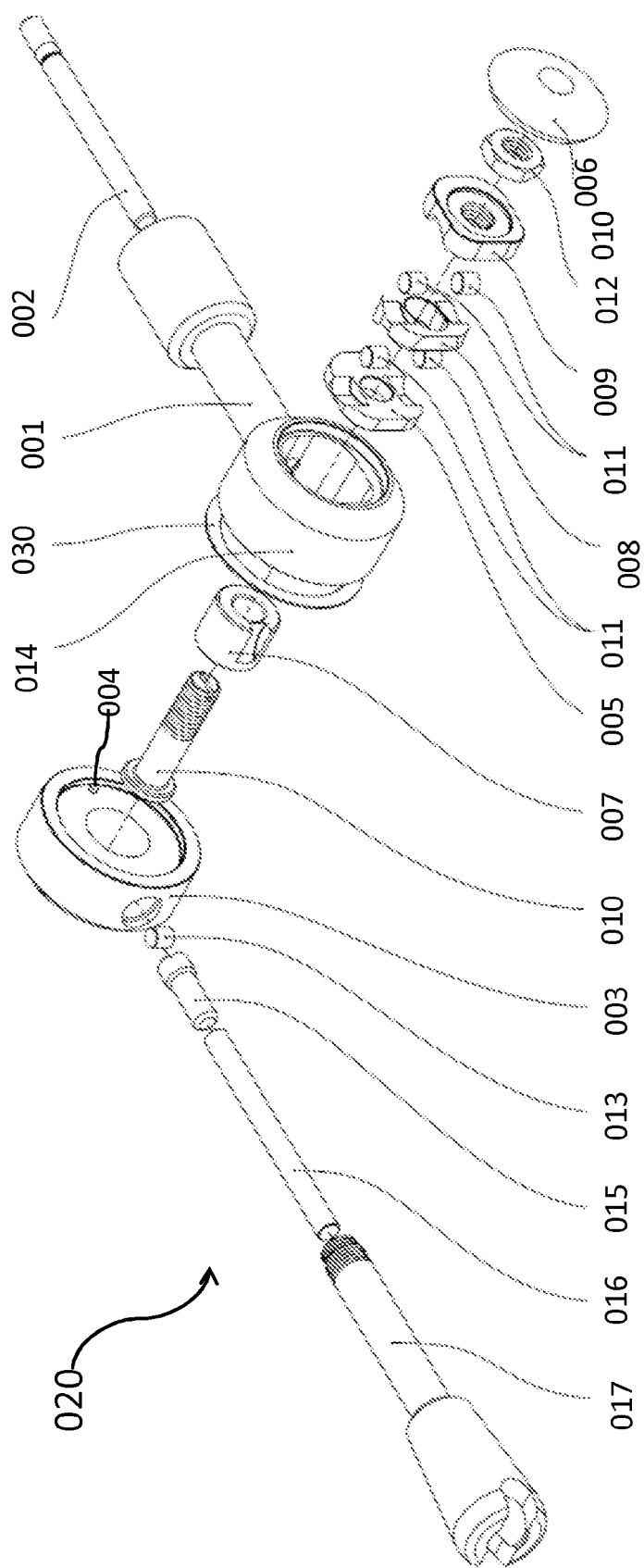
FIG. 3A shows a perspective exploded view of a holding device according to the invention.

FIG. 3A shows an exploded view of an embodiment of the present invention. Here, it is possible to view the two joint halves 003 and 014, and the elements associated therewith, separately. The proximal right joint half 014 has the ramp system with the wedge body 008, while the distal joint half 003 substantially has a ramp socket 007. A sliding disc 030 is arranged between the housing halves 003 and 014. A diamond carbon disc is preferably used in order to allow the joint 021 to rotate with low friction. The rotatability is limited to preferably 340° by means of the anti-rotation pin 004 interacting with a circumferential groove (not shown) running in the distal housing half. The circumferential groove has radially running stop surfaces or the like for the limitation.

On the proximal joint side with the ramp system, a proximal force can be strengthened approximately threefold compared to conventional locking mechanisms, and in this case the path can be reduced to one third. This is particularly advantageous, because in this manner both housing halves can be pressed onto one another with a high force. On the distal side, on the left side here in FIG. 3A, the force of the tightening axis is then in turn deflected by 90° in the distal direction. In the shown embodiment, this deflection is performed by a ramp socket 007, which is connected operatively connected to the thrust element 015 via the sliding body 013.

The shown embodiment of the holding device shows two principles for the transmission of force. On the one hand, this embodiment of the holding device 020 has, on the proximal side, the combination of sliding bodies 011 or rolling bodies with a wedge body 008. On the other hand, a sliding body 013 in connection with a ramp socket 007 is provided on the side of the distal housing half 003. Depending on the desired force/path relationships, these alternatives can be combined with one another as desired. For example, as an alternative to the ramp socket 007, a second wedge body 008 with a ramp system which interacts therewith can be arranged in the distal housing half part 003.

Figure 3B:
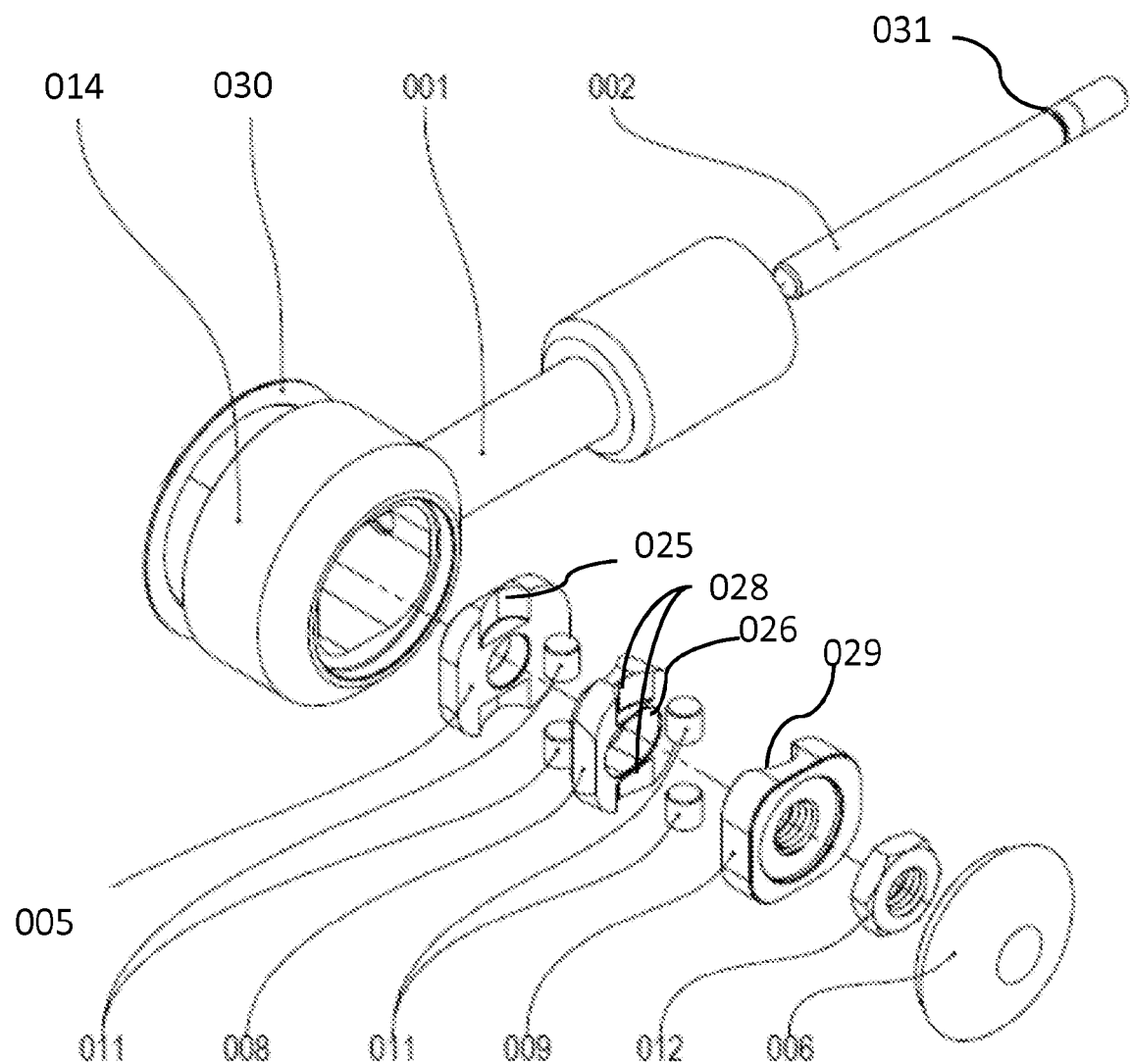
FIG. 3B shows a detailed view of the proximal part of the holding device shown in FIG. 3A, comprising a ramp system.

FIG. 3B shows solely the proximal housing half 014 and the associated components, in order to illustrate details. The base plate 005 is configured as a substantially oval hollow cylinder with a circular through-hole. The proximal base area of the base plate 005 has opposing recesses which are in the shape of parabolic segments and which have curved tracks as base ramp surfaces 025. Ramp surfaces or tracks curved in this manner are likewise realised by the wedge surfaces 028 in the case of the wedge body 008.

The wedge body 008 is likewise configured as a hollow cylinder, the base surfaces of which have said curved wedge surfaces 028. FIG. 3B additionally shows that the through-hole of the wedge body 008 is configured as an elongated hole (026), in order to enable a displacement path of the wedge body 008 both axially and perpendicularly to the tightening axis. Finally, the two wedge surfaces 028 facing the mating plate 009 interact with two mating ramp surfaces 029 of the mating plate 009 via the sliding body 011. The mating ramp surfaces 029 also have curved tracks, like the wedge surfaces 028.

It is advantageous to provide the ramp system in the right or proximal side of the joint housing, as shown in FIG. 3B, since high forces are necessary here to clamp the central joint. In this manner it can be ensured that a locking of the joint takes place reliably. Through the ramp system, small paths can cause very high clamping or locking forces to be conducted onto the central joint. As shown in FIG. 3B, the rolling bodies 011 run in arched and curved tracks to reduce friction and centre automatically. This is advantageous compared to conventional linear bearings and can optimise costs and installation space.

FIG. 3B shows that the thrust element 002 has, at its proximal end, a groove for spring means. Through the use of spring means, a predeterminable residual inhibition can be guaranteed and free holding segments of the holding device or of joints, which are attached to the distal holding segment, can be prevented from flapping around. In operation, the thrust element 002 is plugged at its distal side into the holding segment 001 or the open arm stump and at its proximal side into a coupling device 300 which is illustrated in the following FIG. 4.

Figure 4:
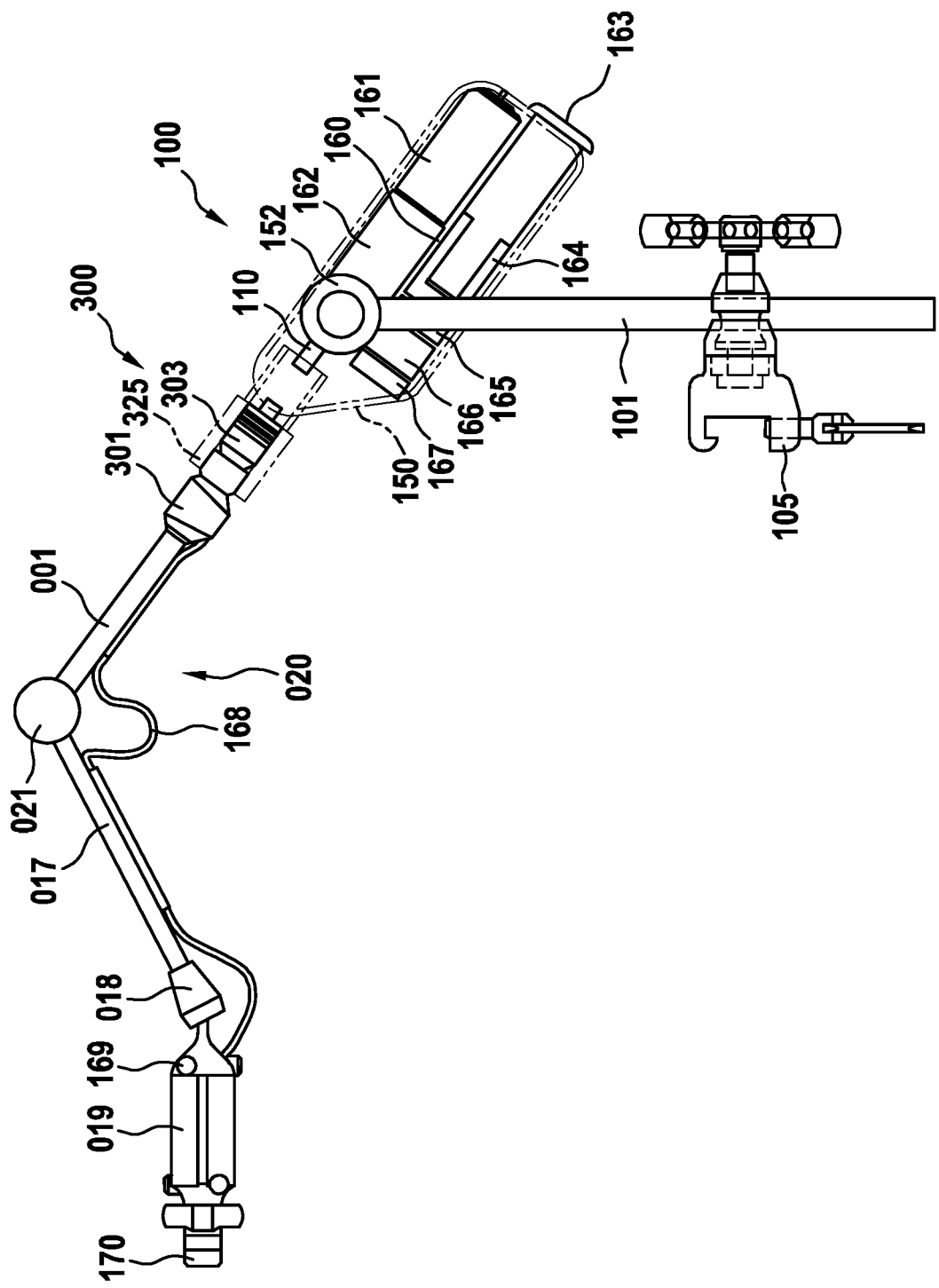
FIG. 4 shows a schematic view of a holding system with a further embodiment of the holding device according to the invention.

FIG. 4 shows a holding system with a holding device 20 according to the invention. At its proximal end, the holding device 20 is connected to a clamping device 100 via a coupling device 300. The base column 101 is located at the base of the holding system. This base column or holding segment 101 is compatible with all existing and commercially customary clamping units 105, so that it can be securely clamped on an operating table. For example, the base column or the holding segment 101 may have a diameter of approximately 16 mm. Depending on a particularly large load capacity, larger diameters up to a maximum of 2 cm can also be provided. The clamping device 100 has a housing 150. For pivotability of the holding segment or base column 101 there is located between the housing of the clamping device 100 and the holding segment 001 a joint 152 which, due to the holding system or holding arm distally attached to the clamping device 100, can also be called a shoulder joint.

The fastening point of the clamping unit 105 for the first holding segment 101 is arranged in the proximal region of the clamping device 100. The proximal region can be located close to the floor or an operating table. The holding system can alternatively be ceiling-supported as opposed to an operating-table-supported system. The distal region of the holding system is the region which is remote from the proximal region. A holding device 20 in the form of a holding arm, with an upper arm and lower arm respectively, is attached to the distal side of the clamping device through a coupling device 300. The attached holding device 20 comprises two holding segments 001 and 017, which are pivotably connected to one another by a central joint 21.

A handle 019 is attached to the distal holding segment 017. A medical instrument, for example, can be attached to the free end of the handle 019 or holding system. For this purpose, the distal end of the handle 019 has a coupling unit 170. This coupling unit 170 can preferably be configured as a rapid-coupling unit such as the known KSLOCK interface. Various medical instruments such as microscissors, forceps, tweezers, punches or the like can be attached to such an autoclavable rapid-coupling unit 170. Accessories for the operation can also be provided, which can be attached to the rapid-coupling unit 170. Thus, a hand rest, for example, can be coupled via the rapid-coupling unit 170. With such a hand rest, the surgeons can keep a steady hand during surgical interventions lasting several hours.

Alongside the connection to the hand joint 018, which is preferably configured as a ball joint, and the rapid-coupling unit 170, the handle has an actuation element 169. The drive unit 160 of the clamping device 100 can be activated by the distal actuation element 169. The control signal for the activation or actuation of the depicted drive spindle 110 can be conducted to the drive unit 160 via the cable 168. The cable 168 is guided partly along the holding segments 017 and 001. The cable is guided, with some play, between the proximal holding segment 001 and the distal holding segment 017, so that the central joint 21 can move freely. The rotatability of the joint is advantageously limited to 340° to protect the cable.

When the cable is guided to the proximal end of the holding segment 001, it enters into the bolt element 301. The introduction of the cable into the bolt element 301 of the coupling device enables the control signals to be passed through to the drive unit 160 via the coupling device 300. The coupling device 300 has inside it suitable contact elements, in order to further conduct the signal, conducted via the cable, to the drive control unit 160. As an alternative to cable-guided activation, radio-controlled triggering of the clamping device 100 is also conceivable.

In the example depicted, the drive unit 160 includes, for the spindle 110, an electric motor 161 with a gear mechanism 162. The power is supplied to the drive unit 160 by a battery 163. The battery 163 is arranged in the battery shaft 164 and is controlled via the battery control unit 165. A drive control unit 166, as well as a switching logic 167, is furthermore located in the housing. The spindle 110 can be driven by means of the gear mechanism 162 of the electric motor 161.

The layout of the thrust elements, holding segments and joints of the holding system conforms to the forces to be conducted and the parts or instruments to be attached. The maximum reach of the holding system and at the same time the highest stress is achieved when the arm is extended horizontally. In this position, the holding system according to the invention can achieve a holding force between at least 3 kg and 5 kg. Example reaches for the entire holding system are between 55 cm and 71 cm. For applications in sterile surroundings, it is necessary to sterilise the holding device 020 and connection parts. Parts of the holding system which are not intended for sterilisation, such as the coupling device and clamping device, can be covered with a suitable sterile cover or drape.

Figure 5:
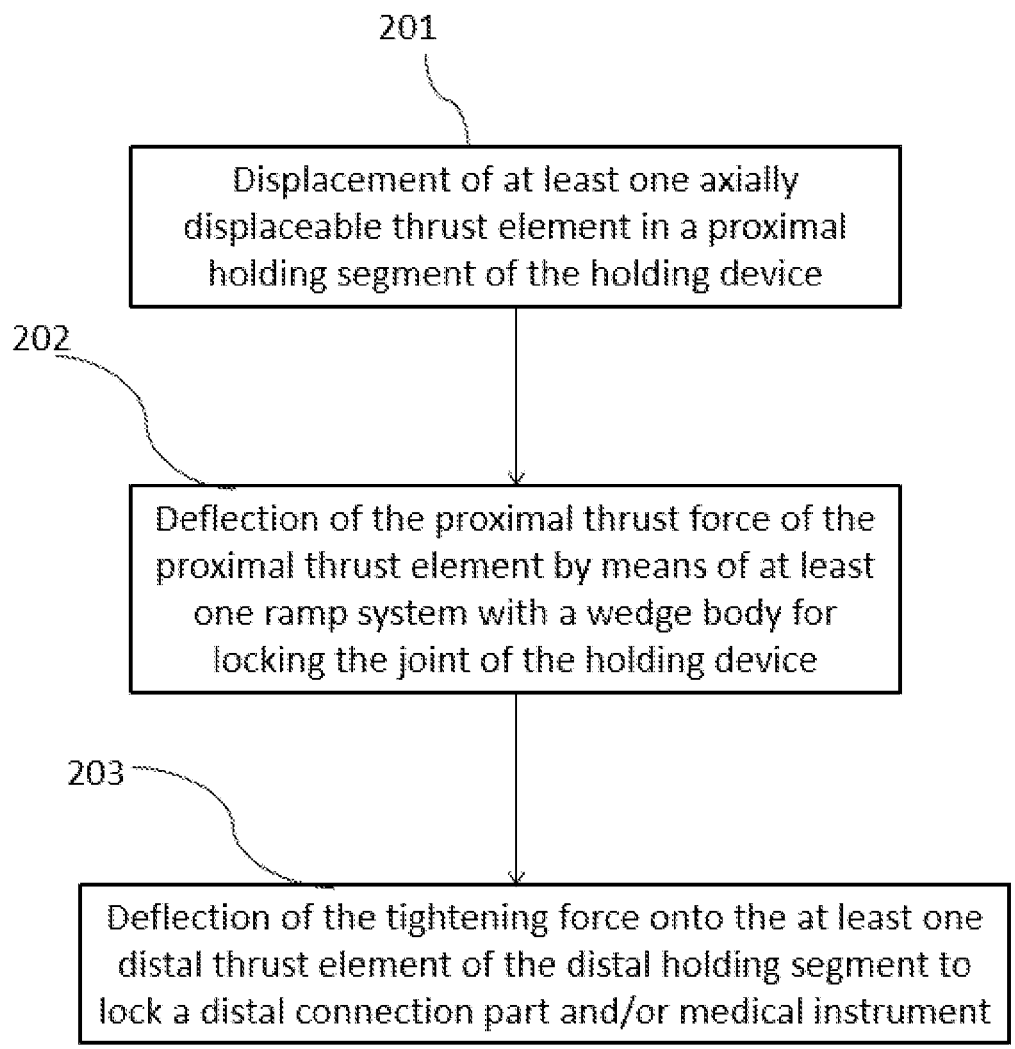
FIG. 5 shows a schematic method diagram for the locking of the joint of the holding device according to the invention.

FIG. 5 shows the significant method steps for locking a joint of a holding device according to the present invention. The first method step comprises displacing at least one axially displaceable thrust element 002 in a proximal holding segment 001 of the holding device 020. The second method step comprises deflecting the proximal thrust force of the proximal thrust element 002 by means of at least one ramp system with a wedge body 008 for locking the joint 021 of the holding device 020. In the further method step 203, the deflection of the tightening force onto the at least one distal thrust element 015, 016 of the distal holding segment 017 takes place to lock a distal connection part and/or a medical instrument. In the aforementioned method, high forces for clamping the joint are advantageously attained with small paths. If the holding device 020 is to be brought from the locking position into the release position, the proximal thrust element 002 can be brought back into the starting position for this purpose.

LIST OF REFERENCE NUMBERS 001 proximal holding segment
002 proximal thrust element
003 distal housing half of the joint
004 securing pin
005 base ramp plate
006 end cap
007 ramp socket
008 wedge body
009 mating plate with mating ramp surfaces
010 tightening bolt
011 sliding body of the ramp system
013 sliding body of the ramp socket
015 thrust element with ramp surface
016 (distal) thrust element
017 (distal) holding segment
018 hand joint
019 handle 020 holding device
021 joint
022 axial longitudinal movement in the distal direction
023 axial movement along the tightening axis in the proximal direction
024 ramp surface of the distal thrust element or ramp ram
025 base ramp surface
026 elongated hole in the wedge body
027 ramp surface of the ramp socket
028 wedge surface
029 mating ramp surface
030 disc
031 groove for spring means
100 clamping device
101 holding segment or base column
105 clamping unit
110 spindle
150 housing of the clamping device
152 joint, base joint
160 drive unit
161 electric motor
162 gear mechanism
163 battery
164 battery shaft
165 battery control unit
166 drive control unit
167 switching logic
168 cable
169 actuation element
170 coupling unit for distal connection part and/or an instrument
201 method step: displacement of a proximal thrust element
202 method step: deflection of the proximal thrust force for locking
203 method step: locking of a distal connection part or a medical instrument
300 coupling device
301 bolt element
303 coupling groove flank
325 coupling actuator

The invention claimed is:

1. A method for locking and releasing a joint of a holding device having two holding segments which are pivotable relative to one another, the method comprising the following steps:
   displacing at least one axially displaceable thrust element in a proximal holding segment;
   deflecting the proximal thrust force of the proximal thrust element onto the tightening axis of the tightening bolt of the joint, in order to lock the joint; and
   deflecting the tightening force onto the at least one distal thrust element of the distal holding segment, in order to lock a distal connection part and/or a medical instrument by displacing the distal thrust element away from the tightening axis; wherein the deflection takes place by deflection elements including at least one ramp system with a wedge body.

2. The method according to claim 1, wherein the at least one ramp system includes: a base plate which is penetrated by a tightening bolt and which has at least one base ramp surface, and a mating plate, which is firmly connected to the tightening bolt and which has at least one mating ramp surface; and
   displacing the wedge body which is acted on by force between the ramp surfaces and moving the mating plate in the direction of the tightening axis relative to the base plate supported on a housing of the joint, and thus to deflect the force by 90 degrees.

3. The method according to claim 1, wherein the component, which is directed perpendicular to the tightening axis, of the displacement path of the wedge body between the release position and the locking position is definable by the length of a central elongated hole of the wedge body.

4. The method according to claim 2, providing a sliding body and engaging at least one base ramp surface and at least one mating ramp surface to each other by the wedge surfaces of the wedge body via the sliding body.

5. The method according to claim 4, wherein the sliding bodies are rolling bodies in the form of spheres, cylinder rollers or barrel rollers.

6. The method according to claim 5, wherein the base ramp and/or the mating ramp each have two at least sectionally cylinder-segment-shaped recesses, which each have a track surface curved towards the respective sliding body as a ramp surface.

7. The method according to claim 1, frictionally locking a distal connection part and/or a medical instrument by displacing at least one distal thrust element.

8. The method according to claim 6, providing a handle having an actuation element and wherein the distal connection part is a hand joint that can be coupled to the handle, and wherein the actuation element is configured to lock or release the joint.

9. The method according to claim 7, wherein the housing of the joint is configured in two parts and the ramp system is arranged in the proximal and/or distal housing half.

10. The method according to claim 1, wherein the holding segments can be pivoted relative to one another via the joint by a pivot angle of up to 340°.

11. The method according to claim 1, wherein the deflection elements further comprise a ramp socket which has a curved ramp surface for a sliding body,
   wherein the ramp socket is rotatably connected to the tightening bolt and is displaceable by displacing the relative location of the tightening bolt along the tightening axis and is engaged with a thrust element via the sliding body in order to deflect force.

12. The method according to claim 1, wherein the thrust elements are configured as one-part or multi-part thrust rods.

13. The method according to claim 11, wherein the thrust element which interacts with the sliding body of the ramp socket has a ramp surface.

14. The method according to claim 13, wherein the proximal housing half comprises the ramp system and the distal housing half comprises the ramp socket with a sliding body configured as a cylindrical or barrel-shaped rolling body.

15. The method according to claim 9, wherein the joint has an end cap which can be removed from the proximal housing half in order to enable a manual displacement of the relative location of the tightening bolt over the proximal end of the tightening bolt.

16. The method according to claim 1, wherein the tightening bolt has, at the proximal end, a thread for a nut which is configured to manually displace the relative location of the tightening bolt.

17. The method according to claim 1, wherein the housing of the joint and/or the holding segments has at least one receptacle for spring means.

18. The method according to claim 1, wherein the proximal holding segment can be connected at its proximal end to a clamping device, by which the thrust element of the proximal holding segment can be displaced to lock and release the joint of the holding device.

19. The method according to claim 18, wherein the holding device and the clamping device can be connected to one another by a coupling device.

20. The method according to claim 18, wherein a cable is guided from a proximal actuation element at a handle, which can be attached to the distal holding segment, along the holding segments, bypassing the joint, and is connected to a drive unit in order to axially displace the proximal thrust element of the holding device by a driveable spindle of the clamping device.

\* \* \* \* \*